United States Patent
Hoffmann

(10) Patent No.: US 6,431,173 B1
(45) Date of Patent: *Aug. 13, 2002

(54) METHOD OF USING ELECTRICAL ENERGY TO PRODUCE TEMPORARY CONDUCTION BLOCK FOR DEFIBRILLATION AND CARDIOVERSION

(75) Inventor: Drew A. Hoffmann, Los Gatos, CA (US)

(73) Assignee: Pacesetter, Inc., Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/487,222
(22) Filed: Jan. 19, 2000

Related U.S. Application Data

(62) Division of application No. 09/022,768, filed on Feb. 12, 1998.

(51) Int. Cl.$^7$ .................................................. H61N 1/39
(52) U.S. Cl. .............................. 128/898; 607/5; 607/101; 606/32
(58) Field of Search .................................. 607/100–102, 607/122, 5, 14; 600/374; 606/32, 34, 27; 128/898

(56) References Cited

U.S. PATENT DOCUMENTS 5,540,681 A 7/1996 Strul et al. ..................... 606/34

(List continued on next page.)

OTHER PUBLICATIONS

Nath, et al., "Basic Aspects of Radiofrequency Catheter Ablation", Journal of Cardiovascular Electrophysiology, vol. 5, No. 10, Oct. 1994, pp. 863–876.

(List continued on next page.)

Primary Examiner—Linda C. M. Dvorak
Assistant Examiner—David M. Ruddy
(74) Attorney, Agent, or Firm—Steven M. Mitchell

(57) ABSTRACT

A method for treating arrhythmias which includes the steps of detecting an arrhythmia, and, in response to detection of the arrhythmia, delivering electrical energy to a targeted part of myocardial tissue in such a manner as to create a transient conduction block in the targeted part of the myocardial tissue without causing permanent damage to the targeted part of the myocardial tissue. The electrical energy can be continuous or pulsed RF, or continuous or pulsed DC. The detected arrhythmia can be atrial fibrillation, atrial flutter, ventricular fibrillation, or other type of arrhythmia. The targeted part of the myocardial tissue constitutes a critical part of the reentrant pathway or reentrant circuit required to sustain the detected arrhythmia. The electrical energy is preferably delivered via a catheter-based electrode which is in direct contact with the targeted part of the myocardial tissue, for either a prescribed period of time or until the arrhythmia is no longer detected (i.e., is terminated). In the former case, the prescribed period of time can be either sufficient to ensure that the arrhythmia can no longer be sustained, or sufficient to ensure that the arrhythmia is organized well enough to be terminated with additional low energy cardioversion/defibrillation therapy (such as a biphasic shock or pulse train). In a first alternative embodiment of the method of the present invention, a shock (or other form of cardioversion or defibrillation therapy) can be delivered, and then, if necessary (e.g., if it is detected that the fibrillation has not been terminated), electrical energy can be delivered to a targeted part of the myocardial tissue in order to create a transient conduction block in the targeted part of the myocardial tissue. In a second alternative embodiment of the method of the present invention, electrical energy is delivered to a targeted part of the myocardial tissue in order to create a first transient conduction block in the targeted part of the myocardial tissue, then a shock (or other form of cardioversion or defibrillation therapy) can be delivered, and then, if necessary (e.g., if it is detected that the fibrillation has not been terminated), electrical energy can again be delivered to the targeted part of the myocardial tissue in order to create a second transient conduction block in the targeted part of the myocardial tissue. The method is preferably carried out by using an automatic implantable defibrillator.

6 Claims, 3 Drawing Sheets

U.S. PATENT DOCUMENTS

| | | | |
|---|---|---|---|
| 5,542,916 A | | 8/1996 | Hirsch et al. .................. 604/22 |
| 5,620,469 A | | 4/1997 | Kroll .............................. 607/7 |
| 5,759,158 A | * | 6/1998 | Swanson ..................... 600/508 |
| 5,868,743 A | | 2/1999 | Saul et al. ..................... 606/49 |
| 6,088,614 A | * | 7/2000 | Swanson ..................... 600/510 |

OTHER PUBLICATIONS

Olgin, et al., "Conduction Barriers in Human Atrial Flutter: Correlation of Electrophysiology and Anatomy", Journal of Cardiovascular Electrophysology, vol. 7, No. 11, Nov. 1996, pp. 1112–1126.

Chen, et al., "Catheter Ablation of Accessory Atrioventricular Pathyways . . . ", American Heart Journal , 8/92 124 (2) 356–65.

Huang, et al., "Chronic Incomplete Atriventricular Block Induced by RF Catheter Ablation", Circulation Oct. 1989 80 (4) 951–61.

* cited by examiner

METHOD OF USING ELECTRICAL ENERGY TO PRODUCE TEMPORARY CONDUCTION BLOCK FOR DEFIBRILLATION AND CARDIOVERSION

"This is a divisional of co-pending application Ser. No. 09/022,768, filed on Feb. 12, 1998."

BACKGROUND OF THE INVENTION

The present invention relates generally to implantable cardioverter-defibrillators, and more particularly, to a method of using electrical energy to produce temporary conduction block in a local region of the patient's myocardium which will disrupt a reentry pathway through which an a trial or ventricular tachycardia (or other type of arrhythmia) is initiated and perpetuated, thereby resulting in cardioversion or defibrillation.

Ventricular fibrillation (VF) has been defined as a "chaotic, random, asynchronous electrical activity of the ventricles due to repetitive re-entrant excitation and/or rapid focal discharge." The resulting uncoordinated excitation and contraction of the ventricles is incapable of pumping blood. Therefore, blood pressure drops rapidly and approaches the mean circulatory pressure within approximately 4–10 seconds. Death generally occurs if the VF is not terminated within 5–10 minutes.

Under normal circumstances, the excitation wave which causes ventricular contraction passes across the ventricle before the myocardial cells become reexcitable (i.e., while the myocardial cells are still refractory and insusceptible to activation). Therefore, the excitation wave dies out and the ventricle remains quiescent until the next impulse arrives through the conduction system. However, if a conduction slowing or block occurs so that cells that have previously been stimulated recover excitability before the excitation wave reaches the area, then repetitive reentrant excitation can occur, leading to VF.

Implantable cardioverter-defibrillators (ICDs) have revolutionized therapy for patients with sustained ventricular tachycardias. ICDs monitor the intrinsic electrical activity of the patient's heart in accordance with a detection or diagnostic algorithm by analyzing electrogram (EGMs) generated by sensing electrodes positioned in the right ventricular apex of the patient's heart. Current-generation ICDs are capable of delivering various types or levels of cardiac therapy, depending upon the type of abnormal cardiac electrical activity which is detected (i.e., depending upon the diagnosis). This capability is commonly referred to in the art as "tiered therapy", the basic idea of which is to "make the punishment fit the crime".

The first type or level of therapy is antitachycardia (also, bradycardia) pacing (ATP), in which a low level of electrical energy (generally between millionths to thousandths of a joule) is delivered to the patient's heart (via a transvenous, non-thoracotomy lead/electrode system) in order to correct detected episodes of tachycardia (or bradycardia). The second type or level of therapy is cardioversion, in which an intermediate level of electrical energy (generally between 1–5 joules) is delivered to the patient's heart (via the lead/electrode system) to terminate a detected episode of ventricular tachyarrhythmia (e.g., a detected heart beat in the range of 130–190 beats/minute) or an ongoing episode of tachycardia that ATP therapy failed to terminate. The third type or level of therapy is defibrillation, in which a high level of electrical energy (generally above 15 joules) is delivered to the patient's heart (via the lead/electrode system) in order to terminate a detected sudden episode of ventricular fibrillation or an episode of ventricular tachycardia which has degraded into ventricular fibrillation due to failure of cardioversion or ATP therapy. The primary goal is to prevent or terminate ventricular tachyarrhythmias in the most efficacious manner while simultaneously minimizing the amount of electrical energy required to do so. This enables the size of the ICD to be minimized and the mean time between replacements of the ICD to be extended, which decreases patient discomfort both at the time of implant and during wear.

Although ICDs have been largely effective for ventricular defibrillation, electrical therapy of complex arrhythmias such as a trial fibrillation is presently difficult. While high energy defibrillation shocks such as those used for ventricular defibrillation are often effective, they produce intolerable pain levels, requiring sedation, if delivered to terminate non-life threatening a trial arrhythmias. Thus, they are impractical for such a trial arrhythmias in an automatic implantable device. Low energy therapies have not yet been realized due to the limited regions of capture associated with point stimulation.

An alternative is ablative therapy. There are two types of ablative therapy, namely, surgical and catheter ablative therapy. The aim of either type of ablative therapy is to permanently destroy (irreversibly damage) the myocardium which constitutes the critical part of the reentrant circuit of the ventricular or a trial tachycardia which is required to sustain or perpetuate the ventricular or a trial tachycardia. In other words, the ablation of the critical region of the myocardium acts to permanently eliminate the conduction or impulse formation through the reentrant pathway which is required to sustain or perpetuate the ventricular or a trial tachycardia. Successful ablation is critically dependent on the ability to localize the involved myocardium necessary to initiate and perpetuate the ventricular or a trial tachycardia. Diagnostic techniques used to localize the reentry circuit include analysis of a 12-lead ECG, catheter mapping during a trial or ventricular tachycardia, and pace mapping. Once the site of origin of ventricular or a trial tachycardia is localized, ablative procedures (surgical or catheter directed) can be performed.

In the catheter ablation approach, catheter-based electrodes are used to permanently disable myocardium tissue adjacent to the electrode without affecting more distant tissue. See, "Basic Aspects of Radiofrequency Catheter Ablation", S. Nath et al., J. Cardiovascular Electrophysiology, Oct. 1994, p. 863, the disclosure of which is incorporated herein by reference, and "Radiofrequency Catheter Ablation of Cardiac Arrhythmias: Basic Concepts and Clinical Applications", DiMarco and Prystowsky, eds., AHA Monograph Series, Futura Publishing Company, NY, 1995, the disclosure of which is also incorporated herein by reference.

Using RF energy (500–1000 kHz, 15–50 W, 100–800 J, 30–75 V rms and 0.1–1 A rms, for 10–60 sec.), tissue extending several mm from the electrode is heated to 65–100° C. This produces permanent lesions that block reentry or disable the AV node. Particularly in the case of atrial fibrillation, specific anatomical structures are often associated with reentry pathways required to sustain arrhythmias. Work is ongoing to develop limited ablation procedures that will permanently block these critical conduction pathways. As a result, the incidence of arrhythmias may decrease and/or the arrhythmias may be better organized, thereby leading to a higher degree of success with low energy shock therapies. One example of a critical isthmus of conduction for atrial flutter cited by Lesh and co-workers, is found in the lower right atrium extending from the inferior vena cava to the coronary sinus ostium bordered by the eustachian ridge (ER) and the tricuspid annulus (TA). See, "Conduction barriers in Human Atrial Flutter", Olgin et al., *JCE*, Vol. 7, Nov. 1996, p. 1112, the disclosure of which is also incorporated herein by reference. Lesh et al. also speculate that any lesion connecting the ER/crista terminals and the TA could interrupt the atrial flutter reentrant circuit. Although the reentrant pathways for AF are more complex and possibly shorter and more numerous, some success has been achieved with the use of multiple lesions to cure AF.

In spite of the advancements in ablative therapy discussed above, there are significant drawbacks and shortcomings of ablative therapy. Namely, in addition to the fact that ablative therapy carries with it a significant mortality and morbidity risk, it produces permanent myocardial damage.

Based on the above and foregoing, it can be appreciated that there presently exists a need in the art for a method for terminating atrial (and ventricular) tachyarrhythmias which overcomes the above-discussed drawbacks and shortcomings of the presently available technology. More particularly, there is a need in the art for a method for terminating atrial (and ventricular) tachyarrhythmias which uses relatively low energy electrical stimuli and does not cause permanent myocardial damage. The present invention fulfills this need in the art.

SUMMARY OF THE INVENTION

The present invention encompasses a method for treating arrhythmias which includes the steps of detecting an arrhythmia, and, in response to detection of the arrhythmia, delivering electrical energy to a targeted part of myocardial tissue in such a manner as to create a transient conduction block in the targeted part of the myocardial tissue without causing permanent damage to the targeted part of the myocardial tissue. The electrical energy can be continuous (e.g., sinusoidal) or pulsed RF, or continuous or pulsed DC. The detected arrhythmia can be atrial fibrillation, atrial flutter, ventricular fibrillation, or other type of arrhythmia. The targeted part of the myocardial tissue constitutes a critical part of the reentrant pathway or reentrant circuit required to sustain the detected arrhythmia. The electrical energy is preferably delivered via a catheter-based electrode which is in direct contact with the targeted part of the myocardial tissue, for either a prescribed period of time or until the arrhythmia is no longer detected (i.e., is terminated). In the former case, the prescribed period of time can be either sufficient to ensure that the arrhythmia can no longer be sustained, or sufficient to ensure that the arrhythmia is organized well enough to be terminated with additional low energy cardioversion/defibrillation therapy (such as a biphasic shock or pulse train).

Further, in a first alternative embodiment of the method of the present invention, a shock (or other form of cardioversion or defibrillation therapy) can be delivered first, and then, if necessary (e.g., if it is detected that the fibrillation has not been terminated), electrical energy can be delivered to a targeted part of the myocardial tissue in order to create a transient conduction block in the targeted part of the myocardial tissue.

In a second alternative embodiment of the method of the present invention, electrical energy is delivered to a targeted part of the myocardial tissue in order to create a first transient conduction block in the targeted part of the myocardial tissue, then a shock (or other form of cardioversion or defibrillation therapy) can be delivered, and then, if necessary (e.g., if it is detected that the fibrillation has not been terminated), electrical energy can again be delivered to the targeted part of the myocardial tissue in order to create a second transient conduction block in the targeted part of the myocardial tissue.

The method of the present invention (any embodiment) is preferably carried out by using an automatic implantable defibrillator.

BRIEF DESCRIPTION OF THE DRAWINGS

These and various other features and advantages of the present invention will be more clearly understood from the following detailed description taken in conjunction with the accompanying drawings, in which.

DETAILED DESCRIPTION OF THE INVENTION

In overview, the present invention is a method for delivering low energy RF or DC shocks from a catheter electrode in contact with myocardial tissue in order to create a point or a line of transient conduction block in a local region of the myocardium which constitutes the critical part of the reentrant circuit of the ventricular or atrial tachycardia which is required to sustain or perpetuate the ventricular or atrial tachycardia, to thereby disrupt the reentry pathway for a long enough period of time to result in defibrillation/cardioversion, or to result in better organization of the arrhythmia, such that it may be terminated by low energy stimuli (i.e., further low energy defibrillation/cardioversion therapy).

Preferably, the method will be carried out by implanting one or more catheter-based electrodes in contact with myocardial tissue in a critical conduction pathway. For example, a catheter could be positioned to span the ER-TA isthmus. Other positions could be determined on the basis of individual patient mapping or transient block evaluations in EP testing, or other techniques which are well-known in the art. The catheter-based electrode(s) used to deliver the electrical energy for creating a transient conduction block in accordance with the method of the present invention can be also used to deliver defibrillation shocks or other cardiac therapy, or alternatively, can be separate electrode(s) dedicated solely to the delivery of the electrical energy for creating a transient conduction block in accordance with the method of the present invention.

Figure 1:
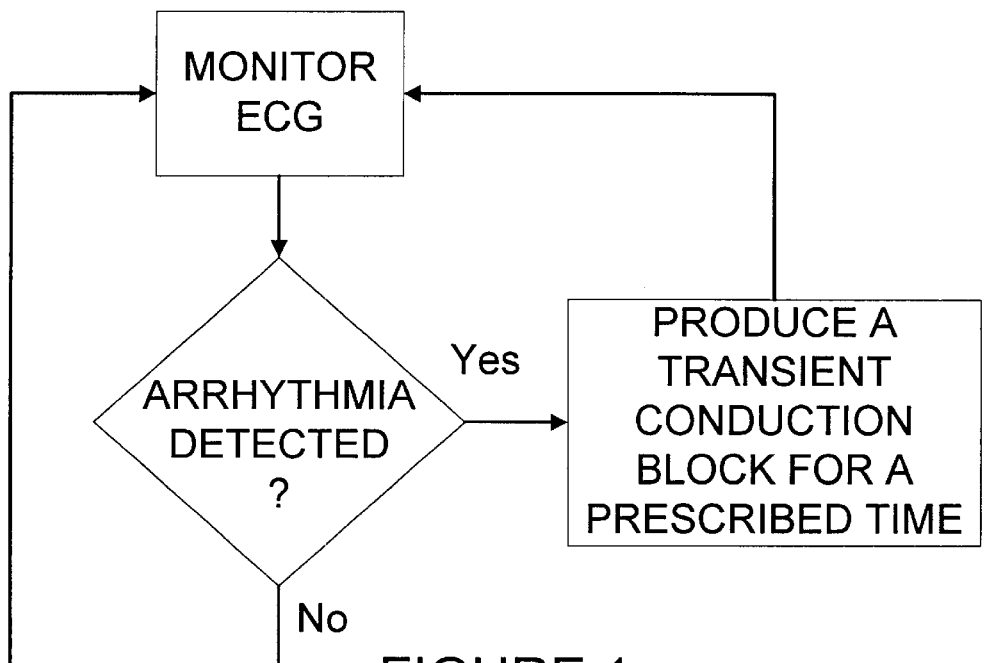
FIG. 1 is a flow chart which illustrates a method according to a first preferred embodiment of the present invention.
Figure 2:
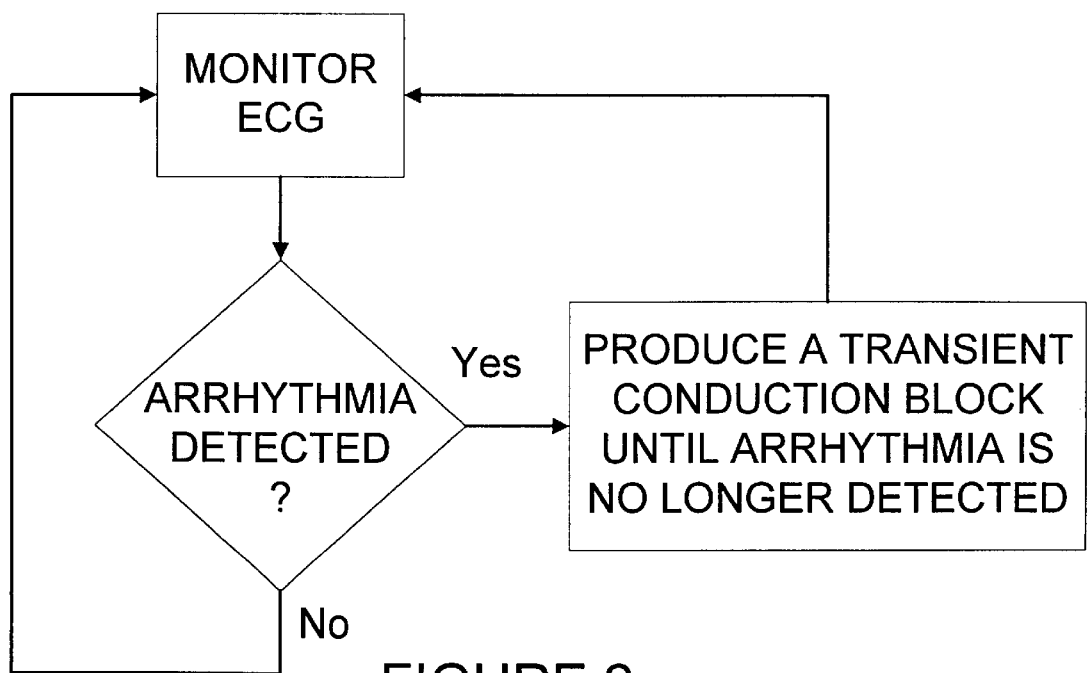
FIG. 2 is a flow chart which illustrates a method according to a second preferred embodiment of the present invention.

With reference now to the flow charts presented in FIGS. 1 and 2, the method of the present invention will now be described in greater detail. More particularly, in accordance with presently preferred embodiments of this invention, when an arrhythmia is detected by the automatic implantable defibrillator in a known manner, a low energy RF, pulsed RF, continuous DC or pulsed DC field will be delivered via the implanted catheter electrode(s) for either a predetermined time period (FIG. 1), or until the arrhythmia is terminated (FIG. 2). In the former case, the predetermined time period can be specified to ensure that the temporary conduction block is maintained long enough so that the arrhythmia can no longer be sustained or perpetuated. Alternatively, the predetermined time period can be specified to ensure that the temporary conduction block is maintained long enough for the arrhythmia to become sufficiently organized to be terminated with additional low energy defibrillation/cardioversion therapy (such as a biphasic shock or pulse train). In any case, the field strength and therapy duration should be chosen to produce transient or temporary conduction block that will disappear after the therapy has been discontinued, so that there is no permanent damage to the myocardial cells.

When applying field stimulation with catheter-based defibrillation electrodes, the goal is to reach a critical current density in the tissue farthest from the electrode. As a result of the decrease in potential gradient with distance from the electrode, very high current densities are produced in tissue closest to the electrode. This can result in conduction block or asystole, requiring back-up bradycardia pacing. In some cases, tissue damage may result as well. By using a strategy in which the tissue targeted for therapy is closest to the electrode, the required shock strength will be reduced.

With the present invention, it is preferred that the catheter electrode used for delivering the electrical energy to the myocardium be in direct contact with the targeted part of the myocardial tissue, thereby greatly reducing the required strength of the electrical energy for blocking the reentrant pathway. It will be appreciated by those skilled in the art that the DC energy can be delivered between the catheter electrode and the pulse generator housing (can) of the ICD, or in any other convenient manner which will be readily apparent to those skilled in the art. Further, although not limiting to the invention, it is preferable that RF energy be used instead of DC energy since it is, at least anecdotally, less painful than DC energy, and further, because RF energy does not electrically stimulate the myocardium in the classical sense of producing activations or graded response (refractory period extension). It will be appreciated by those skilled in the art that the RF energy can be provided by an RF source incorporated within an ICD and can be delivered between the catheter electrode which is in direct contact with the targeted part of the myocardial tissue and the pulse generator housing (can) of the ICD, or between the catheter electrode and one or more other catheter electrodes and/or skin electrodes and/or patch electrodes, or in any other convenient manner which will be readily apparent to those skilled in the art, e.g., using the techniques disclosed in U.S. Pat Nos. 5,540,681 ("Method and system for radiofrequency ablation of tissue") and 5,542,916 ("Dual-channel RF power delivery system"), both of which are incorporated herein by reference. RF energy is alternating current having a frequency of between 30 kHz and 300 MHz. For ablation purposes, the RF energy is typically delivered as a continuous unmodulated sine wave with a frequency of around 500 kHz, although this is not limiting to the present invention. In any case, the field strength and therapy duration should be chosen to produce transient or temporary conduction block that will disappear after the therapy has been discontinued, so that there is no permanent damage to the myocardial cells.

In this connection, it has been demonstrated in animal studies that if tissue is heated to a lower temperature than is required for permanent ablation of the myocardial tissue, a transient loss of excitability of the affected myocardial cells occurs. It has been hypothesized that the mechanism of transient thermal injury involves temporary damage to the cell membrane, resulting in an influx of extracellular sodium and calcium ions, thereby producing depolarization and conduction block. It has also been reported that accessory pathway conduction block may occur after <1 second of RF energy delivery when the tissue temperature is <40° C. It has been suggested that this response is due to a direct electrical effect of the RF field on the cell membrane, producing temporary poration, and thereby increasing membrane permeability, which leads to depolarization.

The method of the present invention provides several advantages over the presently available technology. More particularly, it eliminates or reduces the pain associated with higher energy therapies and does not cause permanent myocardial damage. Moreover, lower energy consumption may lead to smaller device sizes and/or longer mean time between replacements.

It should be clearly understood that the embodiments of the present invention described hereinabove are merely exemplary, and that many other variations and/or modifications of the basic inventive concepts taught herein which may appear to those skilled in the art will still fall within the spirit and scope of the present invention as defined in the appended claims. For example, although it is contemplated that the present invention will have particular utility in atrial defibrillation, it is believed that it will also be useful in terminating ventricular arrhythmias, atrial flutter, and other arrhythmias.

Figure 3:
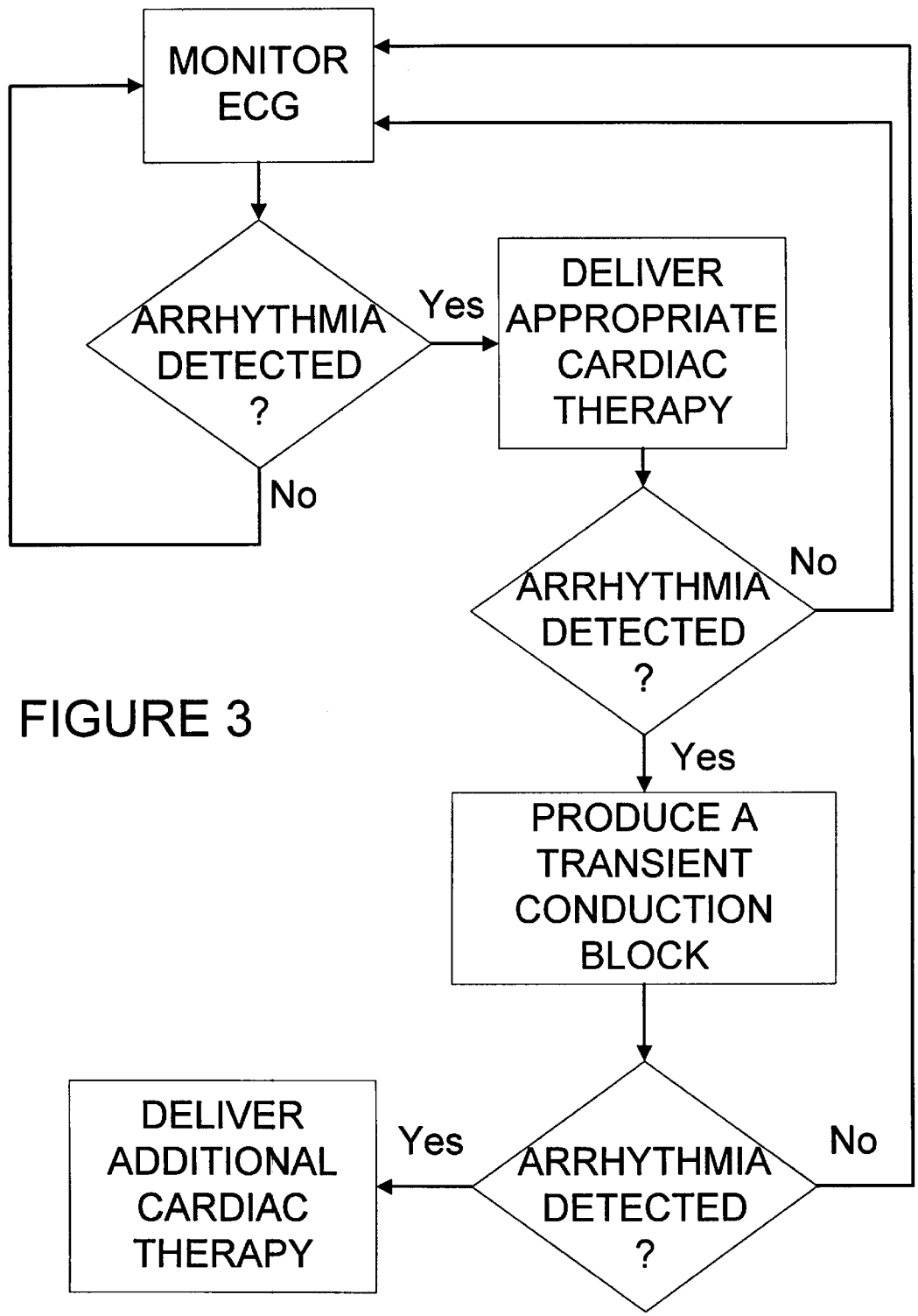
FIG. 3 is a flow chart which illustrates a method according to a first alternative embodiment of the present invention; and, FIG. 4 is a flow chart which illustrates a method according to a second alternative embodiment of the present invention.

Further, with reference now to FIG. 3, in a first alternative embodiment of the method of the present invention, a shock (or other form of cardioversion, defibrillation or other cardiac therapy) can be delivered, and then, if necessary (e.g., if it is detected that the fibrillation or other arrhythmia has not been terminated), electrical energy can be delivered to a targeted part of the myocardial tissue in order to create a transient conduction block in the targeted part of the myocardial tissue. If it is then detected that the arrhythmia has not been terminated, then additional cardiac therapy can be delivered, as appropriate.

Figure 4:
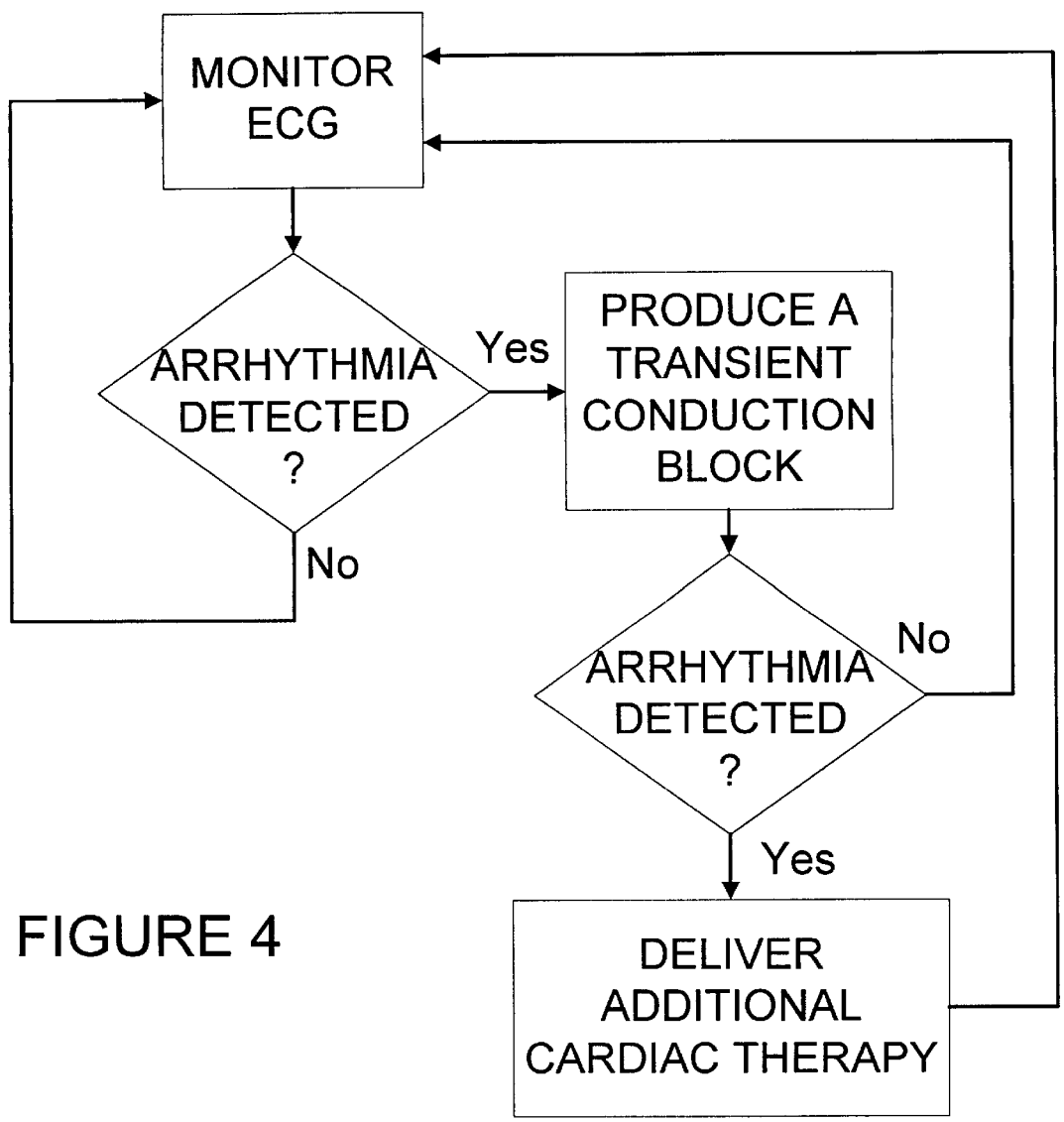

With reference now to FIG. 4, in a second alternative embodiment of the method of the present invention, electrical energy is delivered to a targeted part of the myocardial tissue in order to create a first transient conduction block in the targeted part of the myocardial tissue, then a shock (or other form of cardioversion, defibrillation or other cardiac therapy) can be delivered, and then, if necessary (e.g., if it is detected that the fibrillation has not been terminated), electrical energy can again be delivered to the targeted part of the myocardial tissue in order to create a second transient conduction block in the targeted part of the myocardial tissue. Of course, many other modifications and/or variations are possible.

What is claimed is:

1. A method for treating arrhythmias, comprising the steps of:

detecting an arrhythmia;

in response to detection of the arrhythmia, delivering a cardiac therapy of antitachycardia pacing, cardioversion shock or defibrillation shock to treat the arrhythmia; and, in the event the arrhythmia continues to be detected in spite of the cardiac therapy, delivering electrical energy to a targeted part of myocardial tissue in such a manner as to create a transient conduction block in the targeted part of the myocardial tissue without causing permanent damage to the targeted part of the myocardial tissue.

2. The method as set forth in claim 1, further comprising the step of delivering additional cardiac therapy in the event the detected arrhythmia is not terminated by the transient conduction block.

3. The method as set forth in claim 1, wherein the step of delivering additional cardiac therapy is carried out by delivering one of cardioversion and defibrillation therapy.

4. A method for treating arrhythmias using an implanted medical device, comprising the steps of:

Implanting in a patient the medical device including a detection circuit and a source of electrical energy, the energy source being coupled to delivery means implanted in the region of a targeted part of myocardial tissue;

detecting an arrhythmia with the detection circuit;

in response to detection of the arrhythmia, delivering a cardiac therapy of antitachycardia pacing, cardioversion shock or defibrillation shock to treat the arrhythmia; and, in the event the arrhythmia continues to be detected in spite of the cardiac therapy, delivering electrical energy to the targeted part of myocardial tissue from the energy source through the delivery means in such a manner as to create a transient conduction block in the targeted pat of the myocardial tissue without causing permanent damage to the targeted part of the myocardial tissue.

5. The method as set forth in claim 4, further comprising the step of delivering additional cardiac therapy in the event the detected arrhythmia is not terminated by the transient conduction block.

6. The method as set forth in claim 5, wherein the step of delivering additional cardiac therapy is carried out by delivering one of cardioversion and defibrillation therapy.

* * * * *